(12) United States Patent
Maleeny et al.

(10) Patent No.: US 6,730,311 B2
(45) Date of Patent: May 4, 2004

(54) AIR FRESHENERS COMPRISING POLYURETHANE/POLYUREA MATRICES FOR THE DELIVERY OF FRAGRANCE AGENTS

(75) Inventors: Robert T. Maleeny, Ramsey, NJ (US); James F. Kinney, Ramsey, NJ (US)

(73) Assignee: Scented Technologies, LLC, Mahwah, NJ (US)

( * ) Notice: Subject to any disclaimer, the term of this patent is extended or adjusted under 35 U.S.C. 154(b) by 0 days.

(21) Appl. No.: 10/112,119

(22) Filed: Mar. 30, 2002

(65) Prior Publication Data

US 2003/0017129 A1 Jan. 23, 2003

Related U.S. Application Data

(63) Continuation-in-part of application No. 09/580,265, filed on May 26, 2000, now Pat. No. 6,375,966.

(51) Int. Cl.[7] .......................... A01N 25/00; A61K 9/00; A61K 9/14; A61K 47/32
(52) U.S. Cl. ...................... 424/405; 424/400; 424/486; 514/772.1
(58) Field of Search ................................ 424/405, 400, 424/486; 514/772.1

(56) References Cited

U.S. PATENT DOCUMENTS 5,247,745 A * 9/1993 Valentino ...................... 40/176
5,361,522 A * 11/1994 Green ........................... 40/725
5,409,695 A * 4/1995 Abrutyn et al. ........... 424/70.12

FOREIGN PATENT DOCUMENTS

JP            403146065      * 6/1991

* cited by examiner

Primary Examiner—Thurman K. Page
Assistant Examiner—Blessing Fubara
(74) Attorney, Agent, or Firm—Richard R. Muccino

(57) ABSTRACT

This invention relates to a picture frame assembly comprising (a) a frame panel comprising a sustained release fragrance material; (b) a picture panel comprising an adsorbent panel coated with a fragranced polymeric emulsion; (c) a support panel comprising a fiber board coated with a fragrance oil; and (d) an impervious backing panel. This invention also relates to an air filtration device comprising (a) a frame panel; (b) a porous filtration medium disposed within the frame panel; and (c) an adsorbent panel disposed on the porous filtration medium. A sustained release fragrance material is disposed on a first portion of the adsorbent panel and a fragrance oil is disposed on a second portion of the adsorbent panel.

14 Claims, 3 Drawing Sheets

Figure 1:
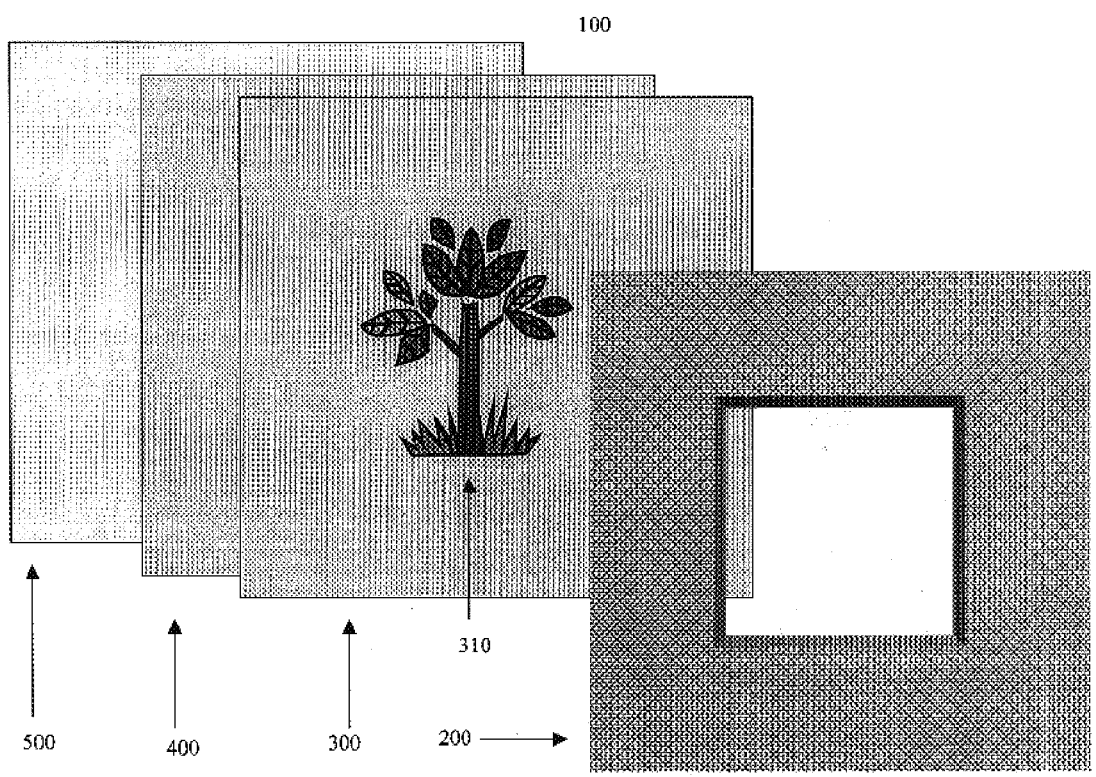

AIR FRESHENERS COMPRISING POLYURETHANE/POLYUREA MATRICES FOR THE DELIVERY OF FRAGRANCE AGENTS

This application is a continuation-in-part of application Ser. No. 09/580,265, filed May 26, 2000 now U.S. Pat. No. 6,375,966.

FIELD OF THE INVENTION

This invention relates to air fresheners, such as picture frame assemblies and air filtration devices, for the delivery of immediate and sustained release fragrance agents.

BACKGROUND OF THE INVENTION

Odor modification is the intentional change of an odor by the addition of a more agreeable odor. Air fresheners are typical odor modifiers because they employ volatile fragrance agents for odor control by altering a malodor to a more pleasant character or to an acceptable level. Air fresheners were initially used in bathrooms and kitchens and consequently have tended to be more functional than attractive. Air fresheners are now used in bedrooms and living rooms and consumers who wish to use air fresheners in these areas of the home may be reluctant to place an unattractive, functional container in these areas.

U.S. Pat. No. 5,247,745 (Valentino) discloses an illuminated picture frame apparatus. The apparatus includes potpourris mounted within the apparatus. Illumination of the apparatus effects heating of the potpourri to direct a scented fragrance about the apparatus.

Polymeric matrices for delivering fragrances or other active agents are known in the art but suffer from the shortcomings of toxicity, cloudiness, instability, and the fractionation of the active components during delivery. Polyurethane/urea elastomers are generally prepared by first reacting an aromatic isocyanate with a polyol to form a prepolymer and then chain extending the prepolymer with an aromatic diamine to form the elastomer. Conventional polymeric matrices for delivering actives generally intermix an active agent into a finished polyurethane/urea elastomer.

U.S. Pat. No. 4,423,099 (Mueller et al.) discloses a non-uniform substantially water-insoluble inter-penetrating polymer blend composition comprising a water-swellable first polymer substrate interpenetrated in a gradient substantially normal to the substrate surface by a less permeable condensation second polymer to form a diffusion rate controlling membrane therein. The water-swellable first polymer may be cellulose or a homopolymer or copolymer containing vinyl alcohol, acrylamide, hydroxyalkylacrylate or methacrylate, vinylpyrrolidone, or hydroxyalkylvinyl ether, maleate, or fumarate or a polyethyleneoxide diol containing polycondensate. The less permeable condensation second polymer may be an aliphatic or aromatic polyurethane, polyester, polyamide, polyimide, polyurea, or polyimine. The compositions are said to be useful as polymers with reduced permeabilities for water and organic solvents and therefore for the controlled delivery of active ingredients such as fragrances and bio-affecting agents into air or aqueous environments, or in membrane separation processes.

U.S. Pat. No. 4,842,761 (Rutherford) discloses a composition for laundering textiles which comprises a detergent composition and a particulate fragrance-bearing polymer comprising a water-soluble normally solid polymer, a water-insoluble normally solid polymer, and a perfume composition. A portion of the perfume composition is incorporated in the water-soluble polymer and a portion is incorporated in the water-insoluble polymer. The water-soluble polymer and the water-insoluble polymer are physically associated with each other such that one is in the form of discrete entities in a matrix of the other. The matrix substantially comprises the surface of the particle. The water-soluble polymer may be a water-soluble polyurethane and the water-insoluble polymer may be a thermoplastic polyurethane. The composition is made by incorporating a perfume composition into a water-soluble polymer, incorporating an olfactory composition into a water-insoluble polymer, intermixing the water-soluble polymer and the water-insoluble polymer under high-shear to provide discrete entities of one polymer in a matrix of the other polymer.

U.S. Pat. No. 4,880,851 (Yamamoto '851) and U.S. Pat. No. 5,075,350 (Yamamoto '350) disclose a method for preparing a composition having a perfume encapsulated in a matrix of polymer. The method comprises adding an acid catalyst for sol-gel methods to an aqueous mixture of alkoxides of metal, silicon, or phosphorus, and a perfume to hydrolyze the alkoxides. A base catalyst for sol-gel methods is added to the reaction mixture to condense the hydrolysate to form a polymer and thereby encapsulate the perfume in the matrix of the polymer. The base catalyst is N,N-dimethylbenzylamine, tributylamine, tri-n-propylamine, tri-pentyl amine, tri-propargyl amine, N,N,N-trimethylethylenediamine, or tri-n-hexylamine, U.S. Pat. No. 4,980,392 (Yamamoto '392) and U.S. Pat. No. 5,387,622 (Yamamoto '622) disclose a method for preparing a composition comprising a perfume encapsulated in a matrix of conjugated polymer. The composition is prepared by adding an acid catalyst for sol-gel methods to a reaction mixture comprising water, an alkoxide selected from metal alkoxides, phosphorus alkoxides, and tetraethoxysilane, a silane coupling agent, and a perfume substance, to hydrolyze the alkoxide and the silane coupling agent, to thereby form a hydrolysate. A base catalyst for sol-gel methods is added to the reaction mixture to condense the hydrolysate to form a conjugated polymer, thereby encapsulating the perfume substance in the matrix of the conjugated polymer.

U.S. Pat. No. 4,987,161 (Yamamoto '161) and U.S. Pat. No. 4,988,744 (Yamamoto '744) disclose a method for preparing a composition comprising a perfume encapsulated in a matrix of conjugated polymer. The method comprises adding an acid catalyst for sol-gel methods to a reaction mixture comprising water, an alkoxide selected from the group consisting of metal alkoxides, phosphorus alkoxides, and tetraethoxysilane, a silane coupling agent, and a perfume substance to hydrolyze the alkoxide, and the silane coupling agent to forming a hydrolysate. An organic monomer selected from the group consisting of acrylic acid, methacrylic acid, dimethyl formamide, acrylonitrile, styrene, methyl acrylate, ethyl acrylate, methyl methacrylate and ethyl methacrylate, is added to the reaction mixture. A base catalyst for sol-gel methods is then added to the reaction mixture followed by irradiating the reaction mixture so that condensation of the hydrolysate occurs with the polymerization of the organic monomer and the hydrolysate of the silane coupling agent to form a conjugated polymer, thereby encapsulating the perfume substance in the matrix of the conjugated polymer.

U.S. Pat. No. 5,093,182 (Ross) discloses a fragrance-releasing, image-displaying article comprising a substrate having deposited thereon a printed image and a fragrance-containing coating composition. The composition comprises an unencapsulated fragrance oil having dissolved therein a sustained-release agent selected from the group consisting of ethyl cellulose, cellulose acetate proprionate, and ethyl hydroxy ethyl cellulose.

U.S. Pat. No. 5,391,420 (Bootman et al. '420) discloses a fragrance-laden pouch for sampling fragrances. The pouch comprises (a) a bottom barrier film member; (b) a top barrier film member joined to the bottom barrier film member to form an enclosure; (c) a fragrance-laden polymer contained within the enclosure in contact with the top and bottom barrier film members; and (d) means for separating the top barrier film member from the bottom barrier film member to permit release of fragrance from the enclosure. The polymer is a modified cellulosic selected from the group consisting of ethyl cellulose, hydroxypropyl cellulose, hydroxyethyl cellulose, methyl cellulose, carboxymethyl cellulose, and the sodium salt of carboxymethyl cellulose.

U.S. Pat. No. 5,569,683 (Bootman et al. '683) discloses a gel comprising a multi-component scented mixture disposed in a polymer matrix comprising the polymerization product of one or more ethylenically unsaturated monomers. The monomers are selected such that the gel has sufficient mechanical integrity to retain its shape under ambient conditions, releases the components of the scented mixture in a manner that substantially preserves the scent of the mixture upon release, and is adapted for incorporation in a container manufactured according to a continuous process in a high speed line. The polymer is derived from an ethylenically unsaturated monomer such as acrylate or methacrylate.

U.S. Pat. No. 5,858,385 (Sirkar et al.) discloses a controlled release device comprising a microporous membrane consisting of a hollow fiber having sealed ends or a film attached to a flat-ended reservoir. The pores extending through the microporous membrane wall are filled with water or an organic solvent and the fiber lumen or reservoir is filled with an organic solvent or water and a selected pest-control substance or fragrance so that the pest-control substance or fragrance in the fiber lumen or reservoir partitions into the water or organic solvent in the pores and diffuses through the water or organic solvent in the pores and out of the microporous membrane.

U.S. Pat. No. 5,965,276 (Shlenker et al.) discloses a latex article having a biocide barrier. The barrier comprises a first layer of cured liquid latex free of biocide, a second layer of a biocide effective as a coagulant for liquid latex, and a third layer of cured liquid latex free of biocide.

U.S. Pat. No. 4,786,703 (Starner et al.) discloses a process for producing a reaction product comprising a prepolymer suited for producing polyurethane/urea elastomers. The method comprises reacting a toluenediisocyanate with a long chain polyol to produce a prepolymer and then reacting the prepolymer with an aromatic diamine to form a polyurethane/urea elastomer. The improvement comprises reacting an isomer of 2,4- or 2,6-toluene diisocyanate with a long chain diol at a temperature from about 0° C. to 90° C., and at a mole ratio of toluenediisocyanate to long chain diol from 4 to 20:1, to form a prepolymer such that at least about 90% of such prepolymer consists of a prepolymer of two moles toluenediisocyanate per mole of long chain diol. Unreacted toluenediisocyanate is then removed from the reaction product to result in a prepolymer level of less than about 0.15%.

While the above disclosures describe air fresheners, none of the above disclosures describe air fresheners that are entirely satisfactory. Moreover, while the above disclosures describe the preparation of polymeric matrices for delivering fragrances, none of the above disclosures describe methods that are entirely satisfactory. None of the above disclosures describe the preparation of polymeric matrices for delivering active agents which incorporate the active in the reaction between a polyurethane prepolymer and a curative amine. The present invention provides such improved polymeric matrices for delivering actives without the disadvantages characteristic of previously known compositions.

IN THE FIGURES

FIG. 1 is a frontal view of a picture frame assembly according to the present invention. The picture frame assembly comprises (a) a frame panel; (b) a picture panel; (c) a support panel comprising a fiber board; and (d) an impervious backing panel. The frame panel comprises a sustained release fragrance material, the picture panel comprises an adsorbent panel coated with a fragranced polymeric emulsion, and the support panel comprises a fiber board coated with a fragrance oil. The picture panel is juxtaposed behind the frame panel, the support panel is juxtaposed behind the picture panel, and the impervious backing panel is juxtaposed behind the support panel.

Figure 2:
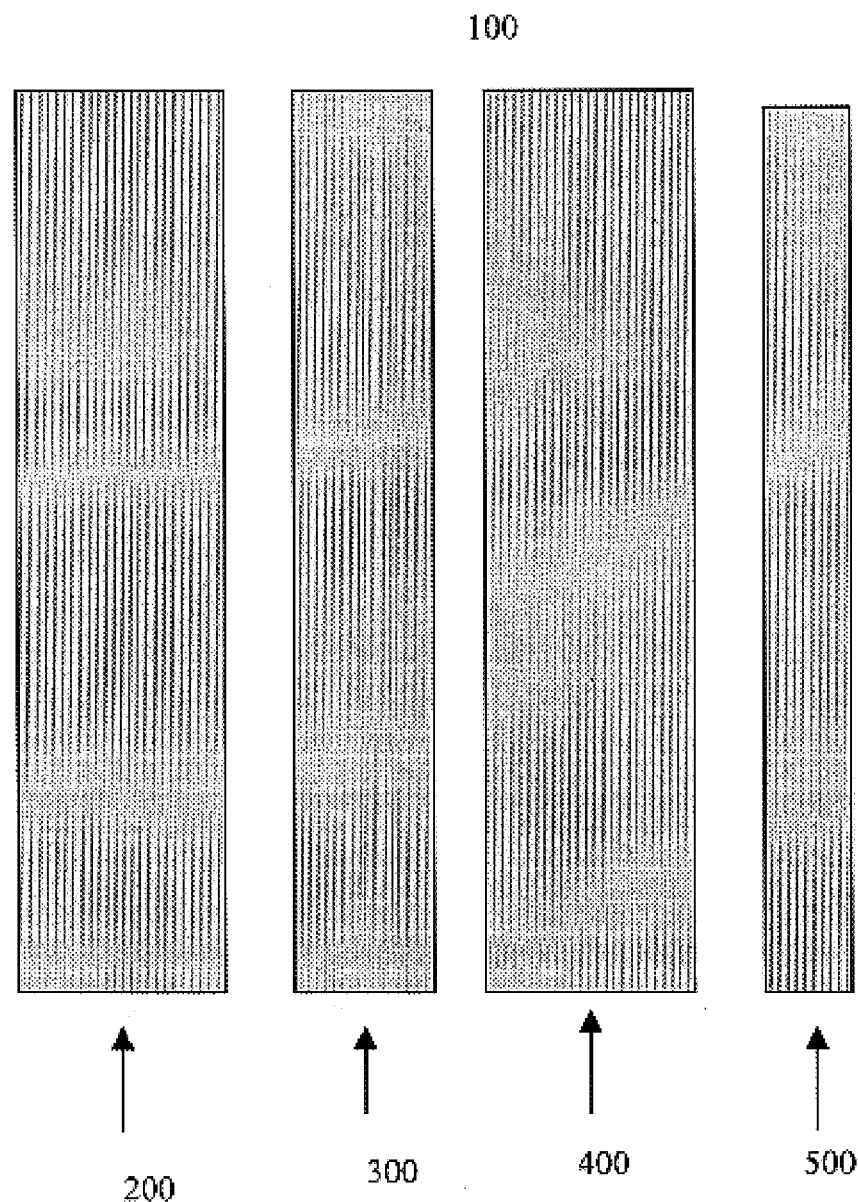

FIG. 2 is a side view of the picture frame assembly illustrated in FIG. 1 according to the present invention.

Figure 3:
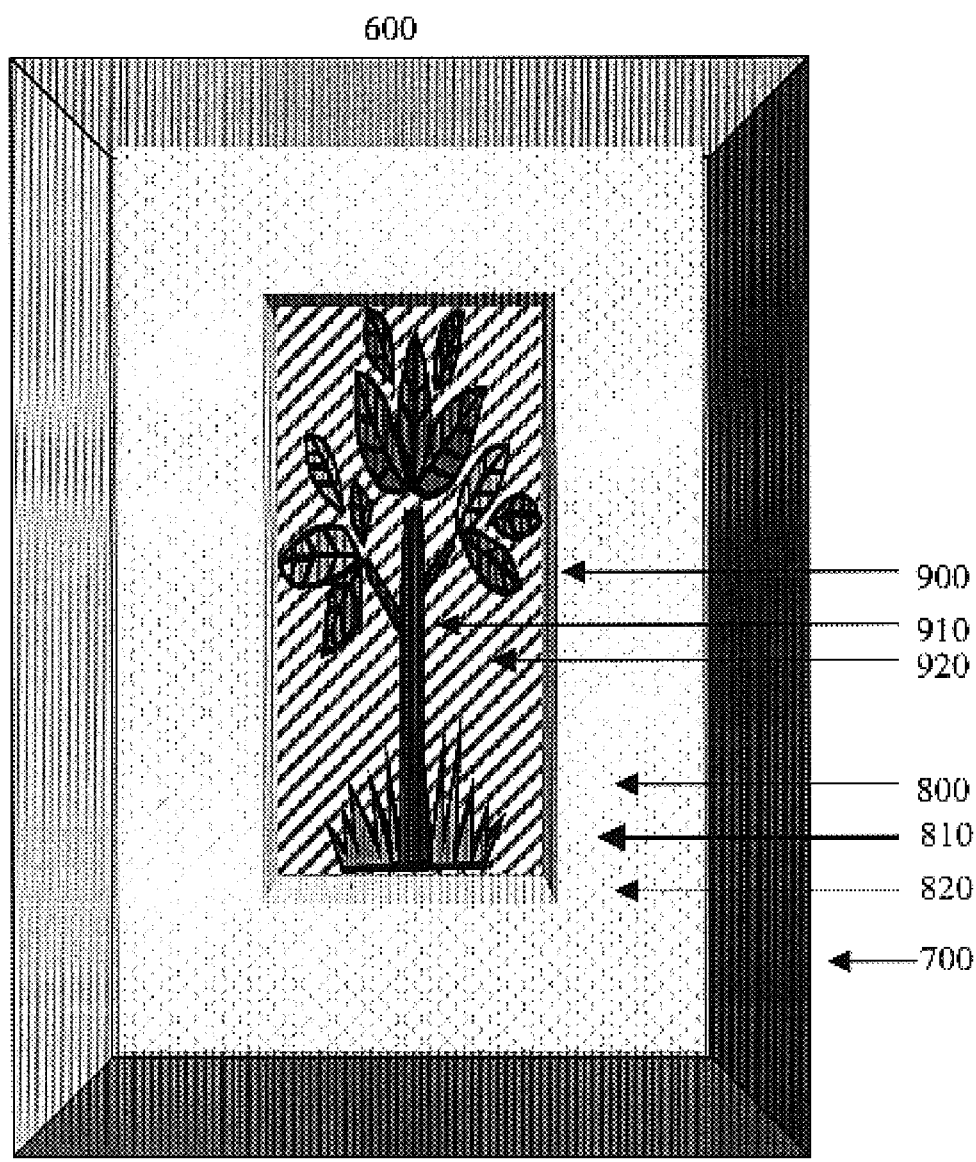

FIG. 3 is a frontal view of an air filtration device according to the present invention. The air filtration device comprises (a) a frame panel; (b) a porous filtration medium disposed within the frame panel; and (c) an adsorbent panel disposed on the porous filtration medium. The adsorbent panel has a first surface for receiving unfragranced air for passage through the panel and a second surface for releasing fragranced air from the panel. A sustained release fragrance material is disposed on a first portion of the adsorbent panel and a fragrance oil is disposed on a second portion of the adsorbent panel.

SUMMARY OF THE INVENTION

The present invention pertains to a picture frame assembly comprising:
 (a) a frame panel comprising, or coated with, a sustained release fragrance material;
 (b) a picture panel comprising an adsorbent panel coated with a fragranced polymeric emulsion;
 (c) a support panel comprising a fiber board coated with a fragrance oil; and
 (d) an impervious backing panel;
wherein the picture panel is juxtaposed behind the frame panel, the support panel is juxtaposed behind the picture panel, and the backing panel is juxtaposed behind the support panel.

The present invention also pertains to an air filtration device comprising:
 (a) a frame panel;
 (b) a porous filtration medium disposed within the frame panel, wherein the porous filtration medium has a first surface for receiving unfiltered air for passage through the medium and a second surface for releasing filtered air from the medium; and
 (c) an adsorbent panel disposed on the porous filtration medium, wherein the adsorbent panel has a first surface for receiving unfragranced air for passage through the panel and a second surface for releasing fragranced air from the panel, wherein a sustained release fragrance material is disposed on a first portion of the adsorbent panel and a fragrance oil is disposed on a second portion of the adsorbent panel.

DETAILED DESCRIPTION OF THE INVENTION

This invention relates to air fresheners, such as picture frame assemblies and air filtration devices, for the delivery of immediate and sustained release fragrance agents. Applicants have discovered that the combination of two or more fragrance diffusion systems, e.g. one floral and one fruity, can produce a sensory impression having extended high levels of activity. The combination of two or more fragrance diffusion systems can be regulated so that a fragrance agent, such as a fragrance oil, is released immediately when an air freshener is first removed from its packaging and then further fragrance agents are released in sustained release from. An organoleptically effective amount of an immediate release fragrance oil can be adsorbed on an adsorbent panel such as a porous absorbent fiberboard (which readily holds liquids), a non-woven polyester, a liquid container (which contains the fragrance oil in liquid form), a solid film (e.g. latex), a solid wax, or other porous material. An intermediate release agent can be employed, such as an aqueous acrylic-urethane hybrid polymer in a dried emulsion dispersion form containing an organoleptically effective amount of a fragrance agent. A long term sustained release fragrance material can be employed such as a polyurethane/polyurea matrix containing an organoleptically effective amount of a fragrance agent. A preferred long term sustained release fragrance material is a polyurethane/urea matrix, prepared by a process of reacting a urethane prepolymer with an aromatic diamine chain extender in the presence of a fragrance agent.

In one embodiment, the present invention pertains to a picture frame assembly comprising (a) a frame panel comprising, or coated with, a sustained release fragrance material; (b) a picture panel comprising an adsorbent panel coated with a fragranced polymeric emulsion; (c) a support panel comprising a fiber board coated with a fragrance oil; and (d) an impervious backing panel. The picture panel is juxtaposed behind the frame panel, the support panel is juxtaposed behind the picture panel, and the backing panel is juxtaposed behind the support panel.

In another embodiment, the present invention pertains to an air filtration device comprising (a) a frame panel; (b) a porous filtration medium disposed within the frame panel, wherein the porous filtration medium has a first surface for receiving unfiltered air for passage through the medium and a second surface for releasing filtered air from the medium; and (c) an adsorbent panel disposed on the porous filtration medium. The adsorbent panel has a first surface for receiving unfragranced air for passage through the panel and a second surface for releasing fragranced air from the panel. A sustained release fragrance material is disposed on a first portion of the adsorbent panel and a fragrance oil is disposed on a second portion of the adsorbent panel.

The term "organoleptic", as used herein, refers to compounds of the invention which stimulate the sense of smell and are thus perceived as having a characteristic odor.

The term "organoleptically acceptable solvent", as used herein, refers to solvents which do not stimulate the sense of smell and are thus perceived as not having a characteristic odor.

The term "organoleptically effective amount", as used herein, means an amount of fragrance compound(s) present in a material at which the incorporated compound(s) exhibit(s) a sensory effect.

The invention will be better understood from the following detailed description of the preferred embodiments taken in conjunction with the Figures, in which like elements are represented by like referenced numerals.

In FIG. 1, a picture frame assembly is depicted generally as 100 and constructed in accordance with a preferred embodiment of the present invention. Picture frame assembly 100 comprises a frame panel 200, a picture panel 300, a support panel 400, and an impervious backing panel 500. Picture frame assembly 100 may be of any shape, for example, circular, oval, triangular, square, rectangular, etc.

Frame panel 200 comprises a sustained release fragrance material. Frame panel 200 may be made of, or coated with, a sustained release fragrance material. In a preferred embodiment, the sustained release fragrance material is a polyurethane/urea matrix. The polyurethane/urea matrix is prepared by a process of reacting a urethane prepolymer with an aromatic diamine chain extender in the presence of a fragrance agent. The aromatic diamine chain extender is selected from the group consisting of 4,4'-methylene-bis(2-chloroaniline), 4,4'-methylene-bis(3-chloro-2,6-diethylaniline), 4,4'-methylene-bis-aniline, diethyltoluenediamine, 5-tert-butyl-2,4-toluenediamine, 3-tert-butyl-2,6-toluenediamine, 5-tert-amyl-2,4-toluenediamine, 3-tert-amyl-2,6-toluenediamine, chlorotoluenediamine, and mixtures thereof.

Picture panel 300 comprises an adsorbent panel coated with a fragranced polymeric emulsion 310. The adsorbent panel may be selected from the group consisting of porous absorbent fiberboards, non-woven polyesters, solid films, and solid waxes. Preferably, the fragranced polymeric emulsion is an aqueous acrylic-urethane hybrid polymer in a dried emulsion dispersion form containing an organoleptically effective amount of a fragrance agent. More preferably, the fragranced polymeric emulsion is Air Products Hybridur 570 Polymer Emulsion containing an organoleptically effective amount of a fragrance agent.

Support panel 400 comprises a fiber board coated with an organoleptically effective amount of a fragrance oil. The fiber board may be composed of cotton, synthetic, or wood fibers with approved wet strength binder products. The fiber board employed may have various densities, colors, thicknesses, and shapes. Preferred fiber boards are those available from Robert Wilson Paper Corp., P.O. Box 540 Lynbrook, N.Y. 11563 under the trade name (caliper/basis wt.) R board (50 pt.), Amaleme (65 and 95 pt.), and AC-5 (85, 100, 125, 440 pt.); and those available from Filter Materials Co., Division of Gusmer Enterprises Inc., P.O. Box 329, Waupaca, Wis. 54981-0339 under the trade name (caliper/thickness) AC-5 (0.230"), AC-5 (0.350"), and AC-5 (0.440").

Impervious backing panel 500 may be an inorganic and organic material. Materials such as polyester (PET), nylon, polyvinylidene chloride (PVdC) and ethylene vinyl alcohol copolymer (EVOH) provide good gas barriers but in many cases poor water vapor barriers. Polythene, polypropylene and ethylene vinyl acetate have gas transmission rates which are too high to maintain a chosen gas mixture for long enough to provide an adequate shelf-life for most products. However, they are good barriers to water vapor and hence prevent products drying out. In order to have a film with a good barrier to both gas and water vapor and the other required properties, it is often necessary to laminate two or more plies together or to co-extrude two polymers. In some cases, a composite film is produced by applying a thin coating of a gas barrier material to a film and then laminating the structure to another film. Typical films for use as impermeable materials are PET laminated to LDPE, or PVdC coated PET laminated to LDPE. Alternatively, EVOH may be co-extruded with linear LDPE. Impervious backing panel is preferably selected from the group consisting of aluminum foil, oxide polyester films (PET), polymer latex films, and laminated films.

Picture panel 300 is juxtaposed behind frame panel 299. Support panel 400 is juxtaposed behind picture panel 300. Impervious backing panel 500 is juxtaposed behind support panel 400.

The frame panel is coated with, or made from, the fragranced polyurethane/polyurea matrices. The inserted picture panel may be printed on an adsorbent panel such as a non-woven material coated with a fragranced polymeric emulsion. A suitable fragranced polymeric emulsion is Hybridur 570 Polymer Emulsion (Air Products) with 20% fragrance agent. Hybridur 570 is an aqueous acrylic-urethane hybrid polymer in an emulsion dispersion form that has been dried. The support panel comprises a fiber board coated with an organoleptically effective amount of a fragrance oil in a free state.

The sensory impression of high and extended strength is further regulated by the incorporation of an impervious backing panel on one side of the air freshener picture frame assembly. The impervious backing panel acts as a barrier to diffusion of the fragrance agent through the covered air freshener. Active diffusion is thus forced in the direction away from the impervious backing panel and as a result appears stronger and lasts longer.

Optionally, an attachment fixture for use in mounting the picture to a wall or some other substrate is included. The fully assembled product is packaged so that fragrance diffusion does not begin until the consumer unwraps the air freshener. When attached to the wall, the impervious backing panel prevents soiling of the wall with fragrance oil and forces fragrance diffusion to the picture side of the air freshener. Fragrance permeates through the non-woven picture and into the air. At the same time, the polyurethane/polyurea fragrance matrices release the same or another fragrance from the frame panel. The combination of a multi diffusion fragrance release system within the same product results in an immediate and long lasting sensory impression.

Polyurethane/polyurea matrices for delivering insect repellents, such as DEET or Citronella, can also be prepared in this manner substituted in whole or in part for the fragrance.

FIG. 2 is a side view of the picture frame assembly 100 depicted in FIG. 1. Picture frame assembly 100 comprises a frame panel 200, a picture panel 300, a support panel 400, and an impervious backing panel 500. Picture panel 300 is juxtaposed behind frame panel 299. Support panel 400 is juxtaposed behind picture panel 300. Impervious backing panel 500 is juxtaposed behind support panel 400.

In FIG. 3, an air filtration device is depicted generally as 600 and constructed in accordance with a preferred embodiment of the present invention. Air filtration device 600 comprises a frame panel 700, a porous filtration medium 800 disposed within the frame panel 700, and an adsorbent panel 900 disposed on the porous filtration medium 880. Air filtration device 600 may be of any shape, for example, circular, oval, triangular, square, rectangular, etc. Preferably, air filtration device 600 is a furnace filtration device or an air conditioning filtration device.

Frame panel 700 contains a porous filtration medium 800 disposed within the frame panel 700. The porous filtration medium 800 has a first surface 810 for receiving unfiltered air for passage through the medium and a second surface 820 for releasing filtered air from the medium. An adsorbent panel 900 is disposed on the porous filtration medium 800. A sustained release fragrance material is disposed on a first portion 910 of the adsorbent panel and a fragrance oil is disposed on a second portion 920 of the adsorbent panel 900.

The adsorbent panel may be decorated with flowers and fruit which are coated with a fragrance agent in a polyurethane/urea matrix. Other portions of the adsorbent panel may be saturated in fragrance oils. The air filtration device is then packaged in a foil wrap. When unwrapped, the air filtration device diffuser system is attached either directly to the air filters, commonly used in furnaces or air conditioning systems, or is suspended in some manner separate from the filter, but within the same air flow channel. When the furnace or air conditioner is activated, the air flow picks up active/fragrance and diffuses it throughout the system.

The fragrance oils employed in the present invention are generally a blend of pleasantly odorous substances (usually liquids) obtained from the essential oils of flowers, leaves, fruit, roots, or wood of a wide variety of plants, either by steam distillation or solvent extraction. Flower oils (rose, jasmine) are extracted with a non-polar solvent to give a waxy mixture called a concrete. The wax is then removed by a second solvent (an alcohol), which is then in turn removed to form an absolute. Fragrance oils are also derived from animal sources (musk, ambergris) and from resinous extracts (terpenes and balsams). Fragrance oils may contain as many as 30 ingredients. Nonlimiting illustrative fragrance oils may be natural products such as ambergris, benzoin, civet, clove leaf oil, galbanum, jasmine absolute, labdanum, mate', melilot, mimosa, musk tonquin, myrrh, mousse de chene, olibanum, opopanax, orris, patchouli, rosemary oil, sandalwood oil, vetivert oil, and violet leaves absolute. Among the various aroma chemicals that may be employed in addition to the foregoing natural products are, for example, acetylated cedarwood terpenes, amylcinnamic aldehyde, amyl salicylate, methyl salicylate, benzyl acetate, benzyl salicylate, p-tert-butylcyclohexyl acetate, citronellol, coumarin, galaxolide, geraniol, hexylcinnamic aldehyde, isobornyl acetate, linalool, linalyl acetate, lyral, musk ambrette, phenethyl alcohol, tetrahydromuguol, and terpinyl acetate.

As set out above, the preferred sustained release fragrance material for use in the frame panel 200 and adsorbent panel 900 of the present invention is preferably a polyurethane/urea matrix. The polyurethane/urea matrix is prepared by reacting a urethane prepolymer with an aromatic diamine chain extender in the presence of an active agent such as a fragrance agent. Urethane prepolymers are prepared from the condensation polymerization of a polyisocyanate and a polyol.

Preferably, the active agent is premixed with the polyisocyanate, premixed with the aromatic diamine chain extender, or premixed with both the polyisocyanate and the aromatic diamine chain extender. The polyurethane/urea matrix may further comprise a solvent for the polyisocyanate, aromatic diamine chain extender, and active agent. The presence of a solvent for the polyisocyanate, aromatic diamine chain extender, and active agent results in the formation of a polyurethane/polyurea elastomer which is clear. The present invention also relates to a process for making the polyurethane/urea matrices as well as to products in which the polyurethane/urea matrices may be incorporated. The improved polyurethane/polyurea matrices for delivering active agents may be cast into various shapes to form consumer products.

A preferred fragranced polyurethane/urea matrix comprises up to about 70% of a fragrance agent using an adduct having a 2:1 ratio of toluene disiocyanate (TDI) and polytetramethylene glycol (PTMEG) with less than 0.1% free isocyanate monomer and one or more aromatic diamine chain extenders such as 4,4'-methylene bis-(2-chloroaniline) (Mboca) or 4,4'-methylene bis-(3-chloro-2,6-diethylaniline) (MCDEA). The polyurethane/polyurea elastomers of the present invention exhibit clarity, hardness, elasticity, sustained release of the fragrance components without fractionation, stability, and versatility in casting a broad range of consumer products at relatively low temperatures.

In one embodiment, the present invention pertains to a polyurethane/urea matrix prepared by a process of reacting a urethane prepolymer with an aromatic diamine chain extender in the presence of an active agent which is a fragrance agent.

The urethane prepolymers of the present invention are those conventionally used in the production of polyurethane compositions. Most commonly, the prepolymer is prepared by the condensation polymerization of a polyisocyanate with a polyol, most preferably the polymerization of a diisocyanate with a diol.

Any suitable organic polyisocyanate may be used such as, for example, ethylene diisocyanate; ethylidene diisocyanate; propylene diisocyanate; butylene diisocyanate; hexamethylene diisocyanate; toluene diisocyanate; cyclopentylene-1,3,-diisocyanate; 3-isocyanatomethyl-3,5,5-trimethylcyclohexyl isocyanate; 3-isocyanatomethyl-3,5,5-trimethylcyclohexyl isocyanate cyanurate; cyclohexylene-1,4-diisocyanate; cyclohexylene-1,2-diisocyanate; 4,4'-diphenylmethanediisocyanate; 2,2-diphenylpropane-4,4'-diisocyanate, p-phenylene diisocyanate; m-phenylene diisocyanate; xylylene diisocyanate; 1,4-naphthylene diisocyanate, 1,5-naphthylenediisocyanate; diphenyl-4,4'-diisocyanate; azobenzene-4,4'-diisocyanate; diphenylsulphone-4,4'-diisocyanate; dichlorohexamethylene diisocyanate; furfurylidene diisocyanate; 1-chlorobenzene-2,4-diisocyanate; 4,4',4"-triisocyanatotriphenylmethane; 1,3,5-triisocyanatobenzene; 2,4,6-triisocyanato-toluene and 4,4'-dimethyldiphenylmethane-2,2',5,5-tetraisocyanate, and the like. Preferably, the polyisocyanate is selected from the group consisting of 2,4-toluenediisocyanate, 2,6-toluenediisocyanate, and mixtures thereof. More preferably, the polyisocyanate is a mixture of 2,4-toluenediisocyanate and 2,6-toluenediisocyanate such that the ratio is adjusted so that the reaction product contains, by weight, from about 75% to about 85% of reacted 2,4-toluenediisocyanate isomer and from about 15% to about 25% of the reacted 2,6-toluenediisocyanate isomer.

Any suitable organic polyol may be used such as, for example, polyhydroxy ethers (substituted or unsubstituted polyalkylene ether glycols or polyhydroxy polyalkylene ethers), polyhydroxy polyesters, the ethylene or propylene oxide adducts of polyols, and the monosubstituted esters of glycerol. Preferably, the polyol is selected from the group consisting of polytetramethylene glycol, polypropylene glycol, and mixtures thereof. More preferably, the polyol is polytetramethylene glycol.

Polyurethane/urea elastomers are prepared by reacting a urethane prepolymer with a chain extender, such as an aromatic diamine chain extender. Examples of aromatic diamine chain extender include 4,4'-methylene-bis(o-chloroaniline), 4,4'-methylene-bis-aniline, diethyltoluenediamine, 5-tert-butyl-2,4 and 3-tert-butyl-2,6-toluenediamine, 5-tert-amyl-2,4- and 3-tert-amyl 2,6-toluenediamine and chlorotoluenediamine. Preferably, the aromatic diamine chain extender is mixture of 4,4'-methylene-bis(2-chloroaniline) and 4,4'-methylene-bis(3-chloro-2,6-diethylaniline).

In a preferred embodiment, the active agent is premixed with the polyisocyanate or the active agent is premixed with the aromatic diamine chain extender. More preferably, the active agent is premixed with both the polyisocyanate and the aromatic diamine chain extender.

The polyurethane/urea matrix may further comprise a solvent for the polyisocyanate, aromatic diamine chain extender, and active agent. Preferably, the solvent is selected from the group consisting of diethyl phthalate, benzyl benzoate, dioctyl adipate, dipropyleneglycol, alcohols, and mixtures thereof. In one embodiment, the active agent is a fragrance agent.

The fragrance agents used in the polyurethane/urea matrices of the present invention are natural perfumes of animal origin or plant origin or synthetic perfumes. The fragrance agents that may be employed include the traditional 5,000+ ingredients used by those skilled in the art of perfumery and flavor development. Illustrative categories of the fragrance agents that may be employed inlude (a) essential oils, (b) absolutes, (c) resins, (d) aromatic chemicals, (e) fixatives, and (f) natural esters. In another embodiment, the active agent is an insect repellant agent such as DEET or Citronella. In a preferred embodiment, the active agent is a mixture of a fragrance agent and an insect repellant agent.

In another preferred embodiment, the mole ratio of polyisocyanate to polyol is maintained at a level from about 6:1 to about 10:1 during the reaction of polyisocyanate with the polyol and the actual reacted isocyanate content, as unreacted NCO in the prepolymer, is at least 95 mole percent of the stoichiometric quantity for a 2:1 molar prepolymer of polyisocyanate and polyol.

The polyurethane/urea matrix may also be in the form of a decorative ornament or a functional product. Functional consumer products include fan blades, air filter grids, and the like, with long lasting air freshener benefits. Preferably, the polyurethane/urea matrix is in the form of a decorative ornament such as a simulated stained glass article. Stained glass articles are made by highly skilled craftsmen and consist of small colored glass panes interconnected by leaded strips. Because of the great skill and the time required to produce stained glass, it is costly and is only used in special situations. It is often desirable to have simulated stained glass made of plastic materials for use in advertising displays, or for decorative panels. To render the simulated stained glass more authentic in appearance, the simulated stained glass should have relief, meaning that portions of the article representing the leaded strips of stained glass should be raised with respect to the areas representing the glass panes, and the areas representing the glass panes should also have relief to represent the irregular type of glass panes normally used in authentic stained glass. Moreover, it is desirable to provide such stained glass articles formed of plastic materials that release pleasant fragrances. Such articles are generally referred to as sun catchers. The preparation of stained glass articles formed of plastic materials is described in detail in U.S. Pat. No. 4,016,235, which disclosure is incorporated by reference herein.

The prepolymers from which the polyurethanes are prepared should have a reacted isocyanate content substantially that of stoichiometric mole ratio of polyisocyanate to polydiol, i.e., a 2:1. This objective is achieved by maintaining a high polyisocyanate to polydiol molar ratio at moderate temperatures. Maintaining a mole ratio of feed polyisocyanate to polydiol is extremely important because when the mole ratio of polyisocyanate to polydiol is lowered to slightly above stoichiometric, e.g., 10% excess, which is conventional, oligomers are formed. Higher oligomer formation results in a lower isocyanate levels in the prepolymer. A lower level of reactive isocyanate in the prepolymer diminishes performance properties in the polyurethane/urea elastomer because it reduces the quantity of diamine chain extender that can be reacted with the prepolymer to produce elastomer hard segment. Although the actual percentage difference between theoretical stoichiometric isocyanate content in prior art systems and actual isocyanate content in prior art systems appears to be small, that difference is substantial in terms of the overall properties imparted to the urethane elastomer.

Ideally in the preparation of a prepolymer for a polyurethane/urea system of this invention the actual isocyanate content should be at least 90%, and preferably at least 95% of the stoichiometric level of isocyanate for a prepolymer having a 2:1 mole ratio of polyisocyanate to polyol. Levels of reacted polyisocyanate below about 95%, and particularly below about 90% of stoichiometric, are direct evidence of polyisocyanate by-product formation and/or oligomer formation.

Temperature also is an important parameter in minimizing oligomer formation in the prepolymer. Typically, as temperature is increased, one must increase the mole ratio of polyisocyanate to polyol. As one approaches the lower end of the mole ratio range of polyisocyanate to polyol, one may experience higher concentrations of oligomer in the prepolymer and subsequently experience decreased properties in the resulting elastomers. On the other hand, as temperature is reduced from a maximum of about 90° C. to a level from 20° C.–40° C., mole ratios of polyisocyanate to polyol can be lowered and molar ratios as low as 4:1 polyisocyanate to polyol can be utilized. However, it is preferred that the mole ratio of polyisocyanate to polyol is from 6 to 10:1 with the reaction being concluded at temperatures from 20° C.–40° C.

Although temperature control has been described as an important parameter in the reaction phase, it must be recognized temperature control is also important in the recovery phase. During removal of unreacted toluenediisocyanate from the prepolymer, the temperature should be maintained as low as possible to avoid reaction of the free polyisocyanate with the prepolymer. Substantial oligomer formation can occur during this removal phase. For this reason if distillation techniques are used to remove free polyisocyanate, a wiped film distillation technique should be considered in order to avoid oligomerization during prepolymer purification.

The exact amount of fragrance agent present in the polyurethane/urea matrix of the present invention is an organoleptically effective amount. An organoleptically effective amount is a level or an amount of fragrance compound(s) present in a material at which the incorporated compound(s) exhibit(s) a sensory effect. The exact amount of fragrance agent is a matter of preference subject to such factors as the particular type of fragrance employed, the polyurethane/urea matrix employed, and the particular end use application. In a preferred embodiment, the fragrance agent is present in the polyurethane/urea matrix in an amount from about 0.5% to about 70%, preferably from about 1% to about 40%, more preferably from about 5% to about 30%, and most preferably from about 10% to about 25%, by weight.

The exact amount of solvent for the polyisocyanate, aromatic diamine chain extender, and active agent present in the polyurethane/urea matrix of the present invention is a matter of preference subject to such factors as the particular type of fragrance employed, the polyurethane/urea matrix employed, and the particular end use application. In a preferred embodiment, the solvent is present in the polyurethane/urea matrix in an amount from about 1% to about 30%, preferably from about 1% to about 20%, more preferably from about 5% to about 15%, and most preferably from about 5% to about 12%, by weight.

In another preferred embodiment, the present invention is directed to a process for preparing a polyurethane/urea matrix. The process comprises reacting a urethane prepolymer with an aromatic diamine chain extender in the presence of an active agent which is a fragrance agent or an insect repellant agent.

The precise formulation of the polyurethane/urea matrix of the present invention will vary depending upon the specific end use. Other ingredients may also be incorporated into the polyurethane/urea matrix as dictated by the nature of the desired composition as well known by those having ordinary skill in the art. While the polyurethane/urea matrix may be used directly as described above, if desired the polyurethane/urea matrix of the present invention may also be formulated with conventional additives such as plasticizers, compatible tackifiers, catalysts, fillers, antioxidants, pigments, mercapto/silane adhesion promoters, stabilizers and the like. The polyurethane/urea matrix compositions are readily prepared using methods generally known in the arts.

Throughout this application, various publications have been referenced. The disclosures in these publications are incorporated herein by reference in order to more fully describe the state of the art.

Throughout this application, applicant will suggest various theories or mechanisms by which applicant believes the components in the adhesive compositions function together in an unexpected manner to provide unique waterborne hot melt agents. While applicant may offer various mechanisms to explain the present invention, applicant does not wish to be bound by theory. These theories are suggested to better understand the present invention but are not intended to limit the effective scope of the claims.

The present invention can be further illustrated by the following examples of preferred embodiments thereof, although it will be understood that these examples are included merely for purposes of illustration and are not intended to limit the scope of the invention unless otherwise specifically indicated.

EXAMPLES

Typical toluene diisocynate (TDI)/aromatic diamine chain extender (curative amine phase), cast elastomer technologies are combined via a manufacturing system which includes separate, pressurized, heated kettles that feed the TDI and amine phases through a proportionating pump system, static mixer and filling head(s). Relatively high temperatures (190° F.–220° F.) are needed to fluidize both phases prior to mixing, reacting and cooling in molds. Once filled, the molded parts are routinely allowed to cool to their Green Temperature, where their basic structures are formed, and then demolded and conditioned at 212° F. for 12–24 hours.

A typical formulation for this type system is set out in Table I.

TABLE I

Typical TDI/Curative Amine Elastomer Formula

| Phase A | |
|---|---|
| TDI Elastomer | 83% |
| Phase B | |
| MOCA (Bisamine A) | 15% |
| Color | 2% |

The stoichiometric relationship between TDI isocyanate Groups and curative amines present dictates many of the physical characteristics of the finished polymer. These are set out in Tables II and III.

TABLE II

Stoichiometry/Ratio of Curative Amine to Isocyanate Groups

| Stoichiometry | Characteristics |
|---|---|
| 85 | Excess NCO Results in Biuret and Allophanate. Highly Crosslinked Lower Limit for Elastomers. |
| 95 | Slightly Crosslinked. Typical Ratio Ratio for TDI-Amines and MDI-Diols. |
| 100 | Almost Linear Polymer. Typical Ratio for TDI-Diols. |
| 105 | Linear Polymer. Best Flex Life and Tear Properties. Upper Limit for Elastomers. |

Applicants have found that certain fragrances could be incorporated into the prepolymer, elastomer/curative amine system without interfering with its reaction kinetics. Cast elastomer polymers can be molded in any shape desired. The resultant polymer produces a significant and easily perceived fragranced effect, which remained very apparent for periods longer than 6 months. The advantages of these new chemistries, versus those where fragrance is added to an already formed polymer, are many. Most notably, the system allows: (a) fragrances to be incorporated into a solid polymer at levels up to and exceeding 70%; (b) The creation of crystal clear, scented polymers in any shape desired; (c) the new polymer/fragrance system forms a novel honeycomb molecular matrix, which allows a sustained release of fragrance for periods, exceeding 6 months; (d) the polymer/fragrance products made with this system do not release liquids in quantities that will stain furniture, clothing or any substrate that comes in contact with the object; (e) the polymer/fragrance system allows production of consumer products at temperatures ranging from 70° F.–220° F.; (f) once formed, the polymer/fragrance system is stable and will not melt at temperatures up to 250° F.; (g) this system allows the addition of insect repellants, colorants, taste modifiers, suspended glitter and objects, flame retardants and many other ingredients useful in achieving functional, attractive, and safe consumer products.

The fragrance agents that may be employed in the polyurethane/urea matrices of the present invention include the traditional 5,000+ ingredients used by those skilled in the art of perfumery and flavor development. Illustrative categories of the fragrance agents that may be employed include (a) essential oils, (b) absolutes, (c) resins, (d) aromatic chemicals, (e) fixatives, and (f) natural esters. A typical formulation in the present invention is set out in Table III.

TABLE III

Scented Polymer Formulation A

| Phase A | |
|---|---|
| TDI/PTMEG Prepolymer | 30–60% |
| Fragrance | 1–30% |
| Phase B | |
| MOCA (Bis-Amine A) 4,4'-Methylene Bis-(2-Chloroaniline) | 8–16% |
| Fragrance | 1–30% |

In addition, the presence of diluents or solvents have been found to be useful. These solvents included diethyl phthalate, benzyl benzoate, dioctyl adipate, dipropyleneglycol, alcohols, and mixtures thereof, and certain oils. Diethyl phthalate, a preferred diluent, also played a significant role as a TDI elastomer viscosity modifier (reduced elastomer viscosity allows better mixing with curative amine phase and thereby better control of reaction kinetics) and solvent for the amine curative phase (allowing it to remain liquid for easier storage and processing). A typical formulation, which employs a diluent like diethyl phthalate is set out in Table IV.

TABLE IV

Scented Polymer Formula B

| Phase A | |
|---|---|
| TDI/PTMEG Prepolymer | 30–60% |
| Fragrance | 1–30% |
| Diethyl Phthalate | 1–30% |
| Phase B | |
| MCDEA Benzamine, 4,4'-methylenebis (3-chloro-2,6-diethyl) | 8–16% |
| Fragrance | 1–30% |
| Diethyl Phthalate | 1–30% |

The inventors further discovered that a unique synergy exists by combining two curative amines referred to as MOCA and Benzamine, 4,4'-methylenebis (3-chloro-2,6-diethyl) as part of the same formulation. When used alone, MOCA formulations are slow reacting and require 3+ hours before a rigid polymer structure is formed. Systems made with MCDEA are quick reacting (30 seconds) and significantly more expensive. The combination of the two curative amines allows for the to production of scented polymers at relatively low temperatures (70° F.–130° F.) and controlled reaction rates (10–90 minutes to Green Temperature). This feature provides a broader range of manufacturing procedures ranging from hand mixing and mold pouring techniques to more sophisticated proportionating pump systems. The lower molding temperatures also allows the use of much less expensive mold construction materials.

Mold materials include PVC, PET, and polycarbonate, as well as more traditional hard rubber or RTV systems. This feature allows a much improved processing system. Specifically, the scented polymer system can be filled into mold designs which also function as a portion of the finished consumer package (e.g. blisterpacks). A typical formula which combines two amine curatives for synergistic processing control is set out in Table V.

TABLE V

Scented Polymer Formula C

| Phase A | |
|---|---|
| TDI/PTMEG Prepolymer | 30–60% |
| Fragrance | 1–30% |
| Diethyl Phthalate | 1–30% |
| Phase B | |
| MOCA | 8–13% |
| MCDEA | 1–4% |
| Fragrance | 1–30% |
| Diethyl Phthalate | 1–30% |
| Additives* | 1–10% |

*Additives may include colorants, ornamental glitter, flame retardants (e.g. Albright & Wilson's Antiblaze 140), taste modifiers (e.g. Bitrex Denatonium Benzoate).

The relationship between the percentage of elastomer and the percentage of curative is known for various stoichiometries (see Table II and III). The curative calculation for a particular TDI elastomer is set out in the following example.

Calculate the parts of MOCA that are theoretically required to cure 100 parts of TDI/PTMEG having an NCO= 6.2% (isocyanate groups/elastomer molecule).

$$\frac{(Stoichiometry)(\% \text{ NCO})}{(Curative\ Equivalent\ Wt.)(Mass\ of\ Prepolymer) - 42.02}$$

$$\frac{(0.95)(0.062)(133.5)(100)}{42.02} = 18.7 \text{ Parts.}$$

When using the curative calculation, shown as Table VI, we can see that the amount of curative needed to react with TDI-prepolymer is directly related to the A) stoichiometry, B) % isocyanate groups (NCO) found within the prepolymer, C) curative equivalent Weight and D) mass of the prepolymer. When evaluating comparative formulations, with various curative amines, the inventors observed significant changes in polymer formation. When testing the following formulation type:

TABLE VI

Scented Polymer Formula D

| Phase A | |
|---|---|
| TDI/PTMEG Prepolymer | 30–60% |
| Fragrance | 1–30% |
| Phase B | |
| Curative Amine | 8–16% |
| Fragrance | 1–30% |

The amines chosen for these studies included:

| Common/Trade Name | Chemical Identification |
|---|---|
| Ethacure 300 | 3,5-dimethlthio-2,6-toluenediamine |
|  | 3,5-dimethylthio-2,4-toluenediamine |
| MOCA (Mboca) | 4,4' methylene bis (2-chloro aniline) |
| Lonzacure MCDEA | 4,4' methylene bis |
|  | (3-chloro-2,6 diethyl aniline) |
| MDA | 4,4' methylene dianiline |
|  | 4,4'-Diaminodiphenylmethane |
| Versalink 740 M | diamine |

The criteria chosen in rating these curative amines included completeness of reaction (polymer formation-hardness) at various time periods after blending Phases A & B and the qualities of the resultant polymers.

Each of the amines performed differently when used alone as the Phase B curative. Ehacure 300 worked well, but was eliminated due to its malodor as a raw material and in the finished product. MOCA performed, but took extended time periods (3–6 hrs.) to react with the TDI elastomer. Lonzacure MCDEA outperformed the other amines in its reactivity with the TDI elastomer and the physical characteristics of the finished polymer. MDA worked well in TDI elastomer reactivity but discolored quickly into a deep amber color. Versalink 740 M did not work under any of the conditions tested. The combinations of 1) MCDEA and MOCA and 2) MDA and MOCA produced an unexpected synergism which allowed full control of the reaction rate (1–60 minutes till polymer solidification) at a lower level of actives than was called for by the chemical equation listed in Table III. This unexpected observations was thought to be do to the stereo chemical configuration of each amine. The MCDEA and MDA appear to have an unhindered configuration, while the MOCA, Ethomeen and Versalink 740 M show evidence of a hindered configuration in cross linking the TDI elastomers. It is theorized, that the combinations of MCDEA and MOCA or MDA and MOCA are synergistic due to a more favorable TDI elastomer orientation, after some MCDEA and MDA links are formed. Once formed, the MOCA finds it easier to link with the partially formed polymer matrix.

Various attempts were also made to find suitable diluents for the fragranced polymer system described above. Diethyl phthalate (DEP) worked best at all concentrations. Substitution of dioctyl adipate for DEP produced an opaque polymer vs. the transparent type seen in prior studies. This opaqueness was thought to relate to a non-compatibility with the elastomer and polymer system. Substitution of dipropylene glycol produced a clear but much softer polymer, which was easily breakable at certain concentrations.

The data set out below represent Brookfield viscosity data of a range of scented polymer Phase A portions. Their significance relates to the ability to pour into molds/suncatcher cavities, where a high degree of definition is required. The two TDI polymers examined are the PHP-75D, which has a NCO of 9 and the PET-95A which has a NCO of 6. In the final composition (after blending Phase A & B), the PHP-75D produces more rigid polymers vs. the PET-95A (this is logical, since the PHP-75D system would have more crosslinks per polymer molecule).

In example No. 1, we show that a blend of 60 parts of PHP-75D and 5 parts of F29803 produces a viscosity of 12,100 cps. After reacting with phase B, this system has poor flow properties (on a relative basis) and entraps more air causing the final product to appear hazy. In examples 2 & 3, the blend is altered first with additional fragrance and then with DEP (diethy phthalate). The blended viscosity drops significantly to approx. 3000 cps. When combined with Phase B, these systems flow more easily into the fine areas of our molds/cavities and release any air entrapped during the mixing process. The resultant polymers are crystal clear. They are also less rigid, but still ideal for scented polymer consumer products.

Examples 4 and 5 illustrate changes that occur when blending the two TDI elastomers 50/50 and when PET-95A is substituted entirely for the PHP-75D. In both cases flow properties are proportionally improved along with final product clarity. Examples 6 & 7 show the viscosity of the controls without any fragrance or DEP added. The final item 8 shows the viscosity of our Phase B blend. This may be important when considering the alterative, that being to use MOCA and/or MCDEA which are pellets or powders at room temperature and must be heated to 160–190 F. to melt.

Viscosity data were taken at 25° C. Generally, the viscosity of these type systems drops in half for each 10° C. rise in temperature.

| | Viscosity Characteristics of Scented Polymer Phases (Brookfield Spindle #4 12 RPM LV#4 500, 25° C.) | | |
|---|---|---|---|
| | Composition | Reading | Viscosity |
| | Phase A | | |
| 1. | 92.3% 60 PHP 75D 5 F29803 | 24.5 | 12,100 cps. |
| 2. | 80.0% 60 PHP 75D 15 F29803 | 6.2 | 3,100 cps. |
| 3. | 80.0% 60 PHP 75D 5 F29803 10 DEP | 5.6 | 2,800 cps. |
| 4. | 92.3% 30 PHP 75D 30 PET 95A 5 F29803 | 16.8 | 8,400 cps. |
| 5. | 92.3% 60 PET 95A 5 F29803 | 12.8 | 6,400 cps. |
| 6. | 100% PHP 75D | 38.6 | 19,300 cps. |
| 7. | 100% PET 95A | 12.5 | 6,250 cps. |
| 8. | Phase B | 0.5 | 250 cps. |

While a number of embodiments of this invention have been represented, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

We claim:

1. A picture frame assembly comprising:
   (a) a frame panel comprising, or coated with, a sustained release fragrance material, wherein the sustained release fragrance material is a polyurethane/urea matrix, prepared by a process of reacting a urethane prepolymer with an aromatic diamine chain extender in the presence of a fragrance agent, wherein the aromatic diamine chain extender is selected from the group consisting of 4,4'-methylene-bis(2-chloroaniline), 4,4'-methylene-bis(3-chloro-2,6-diethylaniline), 4,4'-methylene-bis-aniline, diethyltoluenediamine, 5-tert-butyl-2,4-toluenediamine, 3-tert-butyl-2,6-toluenediamine, 5-tert-amyl-2,4-toluenediamine, 3-tert-amyl-2,6-toluenediamine, chlorotoluenediamine, and mixtures thereof;
   (b) a picture panel comprising an adsorbent panel coated with a fragranced polymeric emulsion, wherein the fragranced polymeric emulsion is an aqueous acrylic-urethane hybrid polymer in a dried emulsion dispersion form containing an organoleptically effective amount of a fragrance agent;
   (c) a support panel comprising a fiber board coated with a fragrance oil; and
   (d) an impervious backing panel;
   wherein the picture panel is juxtaposed behind the frame panel, the support panel is juxtaposed behind the picture panel, and the backing panel is juxtaposed behind the support panel.

2. The picture frame assembly according to claim 1, wherein the adsorbent panel in (b) is selected from the group consisting of porous absorbent fiberboards, non-woven polyesters, solid films, and solid waxes.

3. The picture frame assembly according to claim 1, wherein the fiber board in (c) is selected from the group consisting of cotton, synthetic, and wood fibers.

4. The picture frame assembly according to claim 1, wherein the impervious backing panel in (d) is selected from the group consisting of aluminum foil, oxide polyester films, polymer latex films, and laminated films.

5. The picture frame assembly according to claim 1, wherein the urethane prepolymer is prepared from the condensation polymerization of a polyisocyanate and a polyol.

6. The picture frame assembly according to claim 5, wherein the polyisocyanate in the urethane prepolymer is selected from the group consisting of ethylene diisocyanate; ethylidene diisocyanate; propylene diisocyanate; 3-isocyanatomethyl-3,5,5-trimethylcyclohexyl isocyanate; 3-isocyanatomethyl-3,5,5-trimethylcyclohexyl isocyanate cyanurate; butylene diisocyanate; hexamethylene diisocyanate; toluene diisocyanate; cyclopentylene-1,3,-diisocyanate; cyclohexylene-1,4-diisocyanate; cyclohexylene-1,2-diisocyanate; 4,4'-diphenylmethane diisocyanate; 2,2-diphenylpropane-4,4'-diisocyanate; p-phenylene diisocyanate; m-phenylene diisocyanate; xylylene diisocyanate; 1,4-naphthylene diisocyanate; 1,5-naphthylene diisocyanate; diphenyl-4,4'-diisocyanate; azobenzene-4,4'-diisocyanate; diphenylsulphone-4,4'-diisocyanate; dichlorohexamethylene diisocyanate; furfurylidene diisocyanate; 1-chlorobenzene-2,4-diisocyanate; 4,4',4"-triisocyanatotriphenylmethane; 1,3,5-triisocyanato-benzene; 2,4,6-triisocyanato-toluene; 4,4'-dimethyldiphenylmethane-2,2',5,5-tetraisocyanate, and mixtures thereof.

7. The picture frame assembly according to claim 6, wherein the polyisocyanate is selected from the group consisting of 2,4-toluenediisocyanate, 2,6-toluenediisocyanate, and mixtures thereof.

8. The picture frame assembly according to claim 5, wherein the polyol in the urethane prepolymer is selected from the group consisting of polyalkylene ether glycols, polyhydroxy polyalkylene ethers, polyhydroxy polyesters, ethylene oxide adducts of polyols, propylene oxide adducts of polyols, esters of glycerol, and mixtures thereof.

9. The picture frame assembly according to claim 8, wherein the polyol is selected from the group consisting of polytetramethylene glycol, polypropylene glycol, and mixtures thereof.

10. The picture frame assembly according to claim 1, wherein the aromatic diamine chain extender is mixture of 4,4'-methylene-bis(2-chloroaniline) and 4,4'-methylene-bis (3-chloro-2,6-diethylaniline).

11. The picture frame assembly according to claim 1, wherein the fragrance agent is premixed with the polyisocyanate.

12. The picture frame assembly according to claim 1, wherein the fragrance agent is premixed with the aromatic diamine chain extender.

13. The picture frame assembly according to claim 1, wherein the active agent is premixed with both the polyisocyanate and the aromatic diamine chain extender.

14. A picture frame assembly comprising:
   (a) a frame panel comprising, or coated with, a sustained release fragrance material; wherein the sustained release fragrance material is a polyurethane/urea matrix, prepared by a process of reacting a urethane prepolymer with an aromatic diamine chain extender in the presence of a fragrance agent; wherein the urethane prepolymer is prepared from the condensation polymerization of a polyisocyanate and a polyol; wherein the polyisocyanate is 2,4-toluenediisocyanate or 2,6-toluenediisocyanate; the polyol is polytetramethylene glycol or polypropylene glycol; and the aromatic diamine chain extender is a mixture of 4,4'-methylene-bis(2-chloroaniline) and 4,4'-methylene-bis(3-chloro-2,6-diethylaniline);

(b) a picture panel comprising an adsorbent panel coated with a fragranced polymeric emulsion; wherein the adsorbent panel is a porous absorbent fiberboard; and the fragranced polymeric emulsion is an aqueous acrylic-urethane hybrid polymer in a dried emulsion dispersion form containing an organoleptically effective amount of a fragrance agent;

(c) a support panel comprising a fiber board coated with a fragrance oil; wherein the fiber board comprises wood fibers; and (d) an impervious backing panel; wherein the impervious backing panel is aluminum foil;

wherein the picture panel is juxtaposed behind the frame panel, the support panel is juxtaposed behind the picture panel, and the backing panel is juxtaposed behind the support panel.

* * * * *